US009463007B2

(12) United States Patent
Kleyman

(10) Patent No.: US 9,463,007 B2
(45) Date of Patent: Oct. 11, 2016

(54) ADJUSTABLE HEIGHT PORT INCLUDING RETENTION ELEMENTS

(71) Applicant: Covidien LP, Mansfield, MA (US)

(72) Inventor: Gennady Kleyman, Brooklyn, NY (US)

(73) Assignee: COVIDIEN LP, Mansfield, MA (US)

( * ) Notice: Subject to any disclaimer, the term of this patent is extended or adjusted under 35 U.S.C. 154(b) by 232 days.

(21) Appl. No.: 13/746,470

(22) Filed: Jan. 22, 2013

(65) Prior Publication Data

US 2013/0225933 A1 Aug. 29, 2013

Related U.S. Application Data

(60) Provisional application No. 61/602,101, filed on Feb. 23, 2012.

(51) Int. Cl.
*A61B 17/02* (2006.01)
*A61B 17/34* (2006.01)
*A61B 17/00* (2006.01)

(52) U.S. Cl.
CPC ....... *A61B 17/0218* (2013.01); *A61B 17/3423* (2013.01); *A61B 17/3431* (2013.01); *A61B 2017/00946* (2013.01); *A61B 2017/3429* (2013.01); *A61B 2017/3443* (2013.01)

(58) Field of Classification Search
CPC .............. A61B 17/02; A61B 17/3423; A61B 2017/0212; A61B 2017/0225; A61B 2017/3429; A61B 17/0218; A61B 17/0293; A61B 17/3431; A61B 17/3462; A61B 2017/0287; A61B 2017/3443; A61B 2017/3435
USPC .................................................. 600/201–217
See application file for complete search history.

(56) References Cited

U.S. PATENT DOCUMENTS

| | | | | |
|---|---|---|---|---|
| 5,308,327 A * | 5/1994 | Heaven et al. | ......... | 604/103.09 |
| 5,391,156 A * | 2/1995 | Hildwein et al. | ............. | 604/174 |
| 5,514,133 A * | 5/1996 | Golub | ................ | A61B 17/3423 |
| | | | | 604/175 |
| 5,524,644 A | 6/1996 | Crook | | |
| 5,894,843 A * | 4/1999 | Benetti et al. | ................ | 128/898 |
| 6,002,955 A * | 12/1999 | Willems et al. | .............. | 600/374 |
| 6,033,426 A * | 3/2000 | Kaji | ............................. | 606/213 |
| 6,450,983 B1 | 9/2002 | Rambo | | |
| 6,926,669 B1 * | 8/2005 | Stewart et al. | ............... | 600/439 |
| 6,958,037 B2 * | 10/2005 | Ewers et al. | .................. | 600/208 |

(Continued)

FOREIGN PATENT DOCUMENTS

| | | |
|---|---|---|
| EP | 2308399 A2 | 4/2011 |
| WO | 20060110733 A2 | 10/2006 |
| WO | 2008/121294 A1 | 10/2008 |

OTHER PUBLICATIONS

European Search Report, Application No. EP 13 15 6276 dated Jul. 24, 2014.

(Continued)

*Primary Examiner* — Matthew Lawson
*Assistant Examiner* — Amy Sipp

(57) ABSTRACT

A surgical apparatus for positioning within a tissue tract accessing an underlying body cavity adapts to tissues having different thickness. The surgical instrument includes a proximal portion with at least one bendable structure attached thereto. The at least one bendable structure is configured to fold anywhere along its length. Folding the at least one bendable structure causes the proximal end of the proximal portion to propagate in a distal direction.

18 Claims, 5 Drawing Sheets

(56) References Cited

U.S. PATENT DOCUMENTS

| | | | |
|---|---|---|---|
| 7,033,319 B2 | 4/2006 | Pulford et al. | |
| 7,297,106 B2 | 11/2007 | Yamada et al. | |
| 7,300,399 B2 | 11/2007 | Bonadio et al. | |
| 7,377,898 B2 | 5/2008 | Ewers et al. | |
| 7,520,671 B2 * | 4/2009 | Lantz et al. | 374/158 |
| 7,537,564 B2 | 5/2009 | Bonadio et al. | |
| 7,727,146 B2 | 6/2010 | Albrecht et al. | |
| 7,909,761 B2 * | 3/2011 | Banchieri et al. | 600/208 |
| 8,343,047 B2 | 1/2013 | Albrecht et al. | |
| 8,934,962 B2 * | 1/2015 | Saadat et al. | 600/476 |
| 2002/0002324 A1 | 1/2002 | McManus | |
| 2002/0095160 A1 * | 7/2002 | Bonutti | 606/119 |
| 2002/0183594 A1 * | 12/2002 | Beane et al. | 600/207 |
| 2004/0049099 A1 * | 3/2004 | Ewers et al. | 600/206 |
| 2004/0073090 A1 | 4/2004 | Butler et al. | |
| 2004/0173218 A1 * | 9/2004 | Yamada et al. | 128/856 |
| 2005/0059865 A1 * | 3/2005 | Kahle et al. | 600/206 |
| 2005/0090716 A1 * | 4/2005 | Bonadio et al. | 600/207 |
| 2005/0090717 A1 | 4/2005 | Bonadio et al. | |
| 2005/0192483 A1 * | 9/2005 | Bonadio et al. | 600/208 |
| 2005/0197537 A1 * | 9/2005 | Bonadio et al. | 600/208 |
| 2005/0288656 A1 * | 12/2005 | Koerner et al. | 606/21 |
| 2006/0129165 A1 * | 6/2006 | Edoga | A61B 17/34 606/108 |
| 2006/0149137 A1 | 7/2006 | Pingleton et al. | |
| 2006/0149306 A1 * | 7/2006 | Hart et al. | 606/191 |
| 2007/0088204 A1 * | 4/2007 | Albrecht et al. | 600/208 |
| 2007/0255222 A1 * | 11/2007 | Li et al. | 604/174 |
| 2007/0270654 A1 * | 11/2007 | Pignato et al. | 600/208 |
| 2007/0270882 A1 * | 11/2007 | Hjelle et al. | 606/108 |
| 2008/0021362 A1 | 1/2008 | Fihe et al. | |
| 2008/0319261 A1 * | 12/2008 | Lucini | 600/114 |
| 2009/0069627 A1 * | 3/2009 | Haindl | 600/37 |
| 2009/0076498 A1 * | 3/2009 | Saadat et al. | 606/41 |
| 2009/0093752 A1 * | 4/2009 | Richard | A61B 17/3423 604/24 |
| 2009/0093850 A1 * | 4/2009 | Richard | 606/300 |
| 2010/0106052 A1 * | 4/2010 | Uznanski et al. | 600/562 |
| 2010/0145148 A1 * | 6/2010 | Wenchell | 600/115 |
| 2010/0249521 A1 * | 9/2010 | Shelton et al. | 600/206 |
| 2010/0262080 A1 * | 10/2010 | Shelton et al. | 604/164.09 |
| 2010/0280326 A1 * | 11/2010 | Hess et al. | 600/206 |
| 2011/0092909 A1 * | 4/2011 | Andersson et al. | 604/164.04 |
| 2011/0257637 A1 * | 10/2011 | Timmerman | 606/1 |
| 2012/0101341 A1 * | 4/2012 | Malandain et al. | 600/204 |
| 2012/0130177 A1 * | 5/2012 | Davis | 600/201 |
| 2012/0130183 A1 * | 5/2012 | Barnes | 600/206 |
| 2012/0130184 A1 * | 5/2012 | Richard | 600/208 |
| 2012/0130187 A1 * | 5/2012 | Okoniewski | 600/208 |
| 2012/0157777 A1 * | 6/2012 | Okoniewski | A61B 17/3423 600/201 |
| 2012/0253134 A1 * | 10/2012 | Smith | 600/203 |
| 2012/0253136 A1 * | 10/2012 | Rodrigues, Jr. | 600/208 |
| 2013/0172684 A1 * | 7/2013 | Smith | 600/208 |
| 2013/0190574 A1 * | 7/2013 | Smith | 600/208 |
| 2014/0148901 A1 * | 5/2014 | Anderson et al. | 623/8 |

OTHER PUBLICATIONS

European Search Report Application No. EP 13 15 6286 dated Jul. 18, 2014.

* cited by examiner

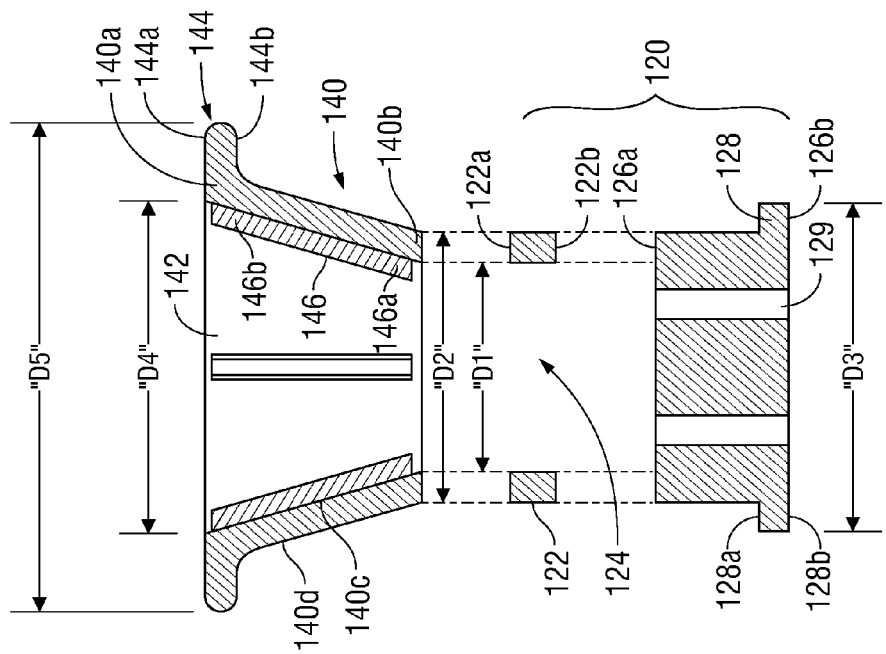
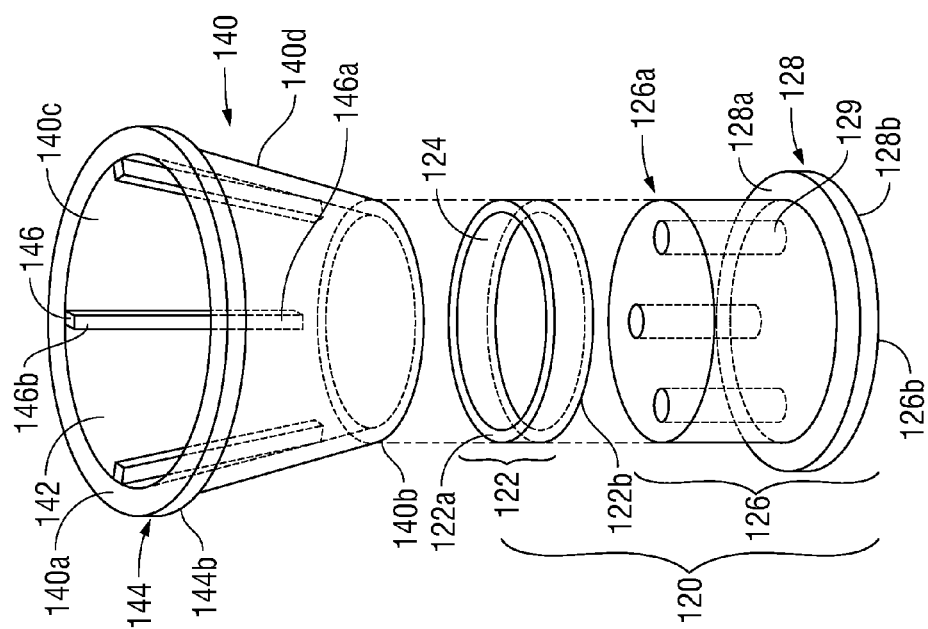

ADJUSTABLE HEIGHT PORT INCLUDING RETENTION ELEMENTS

CROSS REFERENCE TO RELATED APPLICATION

The present application claims the benefit of and priority to U.S. Provisional Application Ser. No. 61/602,101, filed on Feb. 23, 2012, the entire contents of which are incorporated herein by reference.

BACKGROUND

1. Technical Field

The present disclosure relates generally to surgical apparatuses for use in minimally invasive surgical procedures, such as endoscopic and/or laparoscopic procedures, and more particularly, relates to a surgical apparatus that adapts to tissues of different thicknesses.

2. Description of Related Art

Today, many surgical procedures are performed through small incisions in the skin, as compared to large incisions that are typically required in traditional procedures, in an effort to reduce trauma to the patient and reduce the patient's recovery time. Generally, such procedures are referred to as "endoscopic", unless performed on the patient's abdomen, in which case the procedure is referred to as "laparoscopic." Throughout the present disclosure, the term "minimally invasive" should be understood to encompass both endoscopic and laparoscopic procedures.

During a typical minimally invasive procedure, surgical instruments, such as endoscopes, graspers, staplers and forceps, are inserted into the patient's body through the incision in tissue. In general, prior to the introduction of the surgical object into the patient's body, insufflation gas is supplied to the target surgical site to enlarge its surrounding area and create a larger, more accessible work area. This is accomplished with a substantially fluid-tight seal that maintains the insufflation gas at a pressure sufficient to inflate the target surgical site.

Different patients or different target surgical sites have different tissue thicknesses. For that reason, it is desirable to have the substantially fluid-tight seal adjustable to accommodate different tissue thicknesses. It is also desirable to maintain the substantially fluid-tight seal at its adjusted position throughout the entire course of a surgical procedure. Further, it is desirable to increase ease of use or increase maneuverability of multiple instruments that are simultaneously operated through the substantially fluid-tight seal.

The existing access devices in the prior art such as wound retractors may accomplish one objective addressed above but fails to meet all the other objectives. For instance, wound retractors may be adapted to tissues of different thicknesses, but are also known for their drawbacks such as difficult placement, cumbersome use and failure to maintain the insufflation gas at a desired pressure.

Based on the above, a continuing need exists for an access device with increased flexibility to accommodate tissues of different thicknesses, enhanced stability at an adjusted position corresponding to a particular tissue thickness, and improved ability to provide greater freedom of movement of surgical instruments.

SUMMARY

Disclosed herein is a surgical apparatus for positioning within a tissue tract accessing an underlying body cavity. The surgical apparatus includes a proximal portion, a distal portion disposed distally with respect to the proximal portion. The surgical apparatus further includes at least one bendable structure attached to the proximal portion extending between a first end and a second end of the proximal portion.

In one embodiment, the proximal portion defines a generally frustoconical configuration.

In a certain embodiment, the at least one bendable structure is configured to fold along its length. The at least one bendable structure is made from a bendable material comprising metal or plastic. The at least one bendable structure is in the form a rib, strip or tube. Folding the at least one bendable structure causes the first end of the proximal portion to propagate in a distal direction.

In some embodiments, the surgical apparatus includes a plurality of bendable structures.

In one embodiment, the at least one bendable structure is attached to the proximal portion by adhesive or by an overmolding process.

In another embodiment, the proximal portion defines at least one pocket to detachably receive the at least one bendable structure.

DESCRIPTION OF THE DRAWINGS

The above and other aspects, features, and advantages of the present disclosure will become more apparent in light of the following detailed description when taken in conjunction with the accompanying drawings in which:

FIG. 2A is an exploded view of the surgical apparatus of FIG. 1 illustrating a distal portion and a proximal portion;

FIG. 2B is a side cross-sectional view of the surgical apparatus of FIG. 2A;

DETAILED DESCRIPTION

Figure 1:
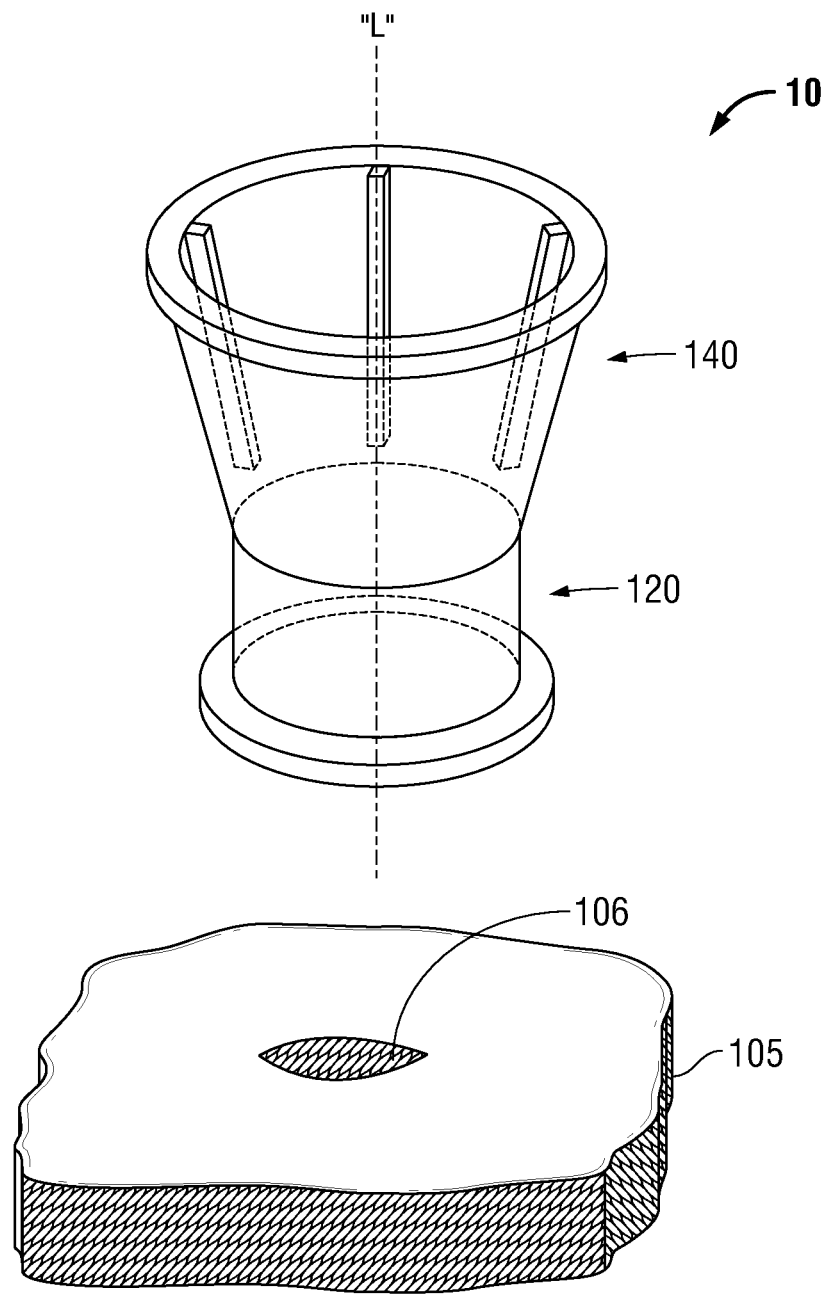
FIG. 1 is a front perspective view of a surgical apparatus in accordance with the principles of the present disclosure illustrating a surgical apparatus positioned relative to the tissue.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

One type of minimally invasive surgery described herein employs a device that facilitates multiple instrument access through a single opening in tissue. This is a minimally invasive surgical procedure, which permits a user to operate through a single entry point, typically the patient's navel. Additionally, the presently disclosed device may be used in a procedure where a naturally occurring orifice (e.g. vagina or anus) is the point of entry to the surgical site. The disclosed procedure involves insufflating the body cavity and positioning a portal member within, e.g., the navel of the patient. Instruments including an endoscope and additional instruments such as graspers, staplers, forceps or the like may be introduced within a portal member to carry out the surgical procedure. An example of such a surgical portal is disclosed in U.S. patent application Ser. No. 12/244,024, Pub. No. US 2009/0093752 A1, filed Oct. 2, 2008, the entire contents of which are hereby incorporated by reference herein.

Referring now to the drawings, in which like reference numerals identify identical or substantially similar parts throughout the several views, FIG. 1 illustrates a surgical apparatus 10 in accordance with the principles of the present disclosure. The surgical apparatus 10 is adapted for insertion in a tissue opening 106 within a tissue tract 105, e.g., through the abdominal or peritoneal lining in connection with a laparoscopic surgical procedure. The surgical apparatus 10 will be described in greater detail hereinbelow.

As shown in FIG. 1, the surgical apparatus 10 is a unitary structure having a distal portion 120 and a proximal portion 140 which are axially aligned along a longitudinal axis "L."

With reference to FIGS. 2A-2B, the distal portion 120 includes a ring member 122 and a base member 126. The ring member 122 generally exhibits an annular configuration, defining an inner diameter of "D1," an outer diameter of "D2," a proximal end 122a and a distal end 122b. The ring member 122 defines a cylindrically-shaped free space 124 therein.

The base member 126 is disposed distally with respect to the ring member 122. The base member 126 defines a proximal end 126a and a distal end 126b, and includes a distal annular flange 128 extending radially outwardly from the distal end 126b. The proximal end 126a defines a radial dimension "D2" identical to the outer diameter of the ring member 122. The distal annular flange 128 defines an outer diameter of "D3" which is greater than the radial dimension "D2" of the ring member 122. The distal annular flange 128 includes a proximal surface 128a and a distal surface 128b. The distal annular flange 128 is configured to be disposed beneath the tissue tract 105, such that the proximal surface 128a abuts the lower side of the tissue tract 105 to securely anchor the surgical apparatus 10 within the tissue tract 105. The base member 126 defines at least one longitudinal passage 129 extending from the proximal end 126a to the distal end 126b. The longitudinal passage 129 is rendered of a size that permits a surgical instrument passing therethrough and forms a sealing relationship with the surgical instrument. In some embodiments, the base member 126 defines a plurality of longitudinal passages 129.

It is envisioned that the ring member 122 and the base member 126 in their entireties are insertable into the tissue opening 106.

With continued reference to FIGS. 2A and 2B, the proximal portion 140 exhibits a generally frustoconical configuration and defines a generally frustoconical-shaped free space 142 therein. The proximal portion 140 defines a proximal end 140a (or a first end 140a), a distal end 140b (or a second end 140b), an inner surface 140c and an outer surface 140d. The proximal portion 140 is mounted proximally with respect to the ring member 122 such that the distal end 140b of the proximal portion 140 abuts the proximal end 122a of the ring member 122. The distal end 140b has the same radial dimension as that of the intermediate member 122, such that the distal end 140b defines an inner diameter of "D1" and an outer diameter of "D2." The proximal portion 140 includes a proximal annular flange 144 extending radially outwardly from the proximal end 140a of the proximal portion 140. The proximal end 140a defines an inner diameter "D4" which is substantially greater than the inner diameter "D1" of the distal end 140b. The proximal annular flange 144 defines an outer diameter "D5" which is substantially greater than the outer diameter "D3" of the distal annular flange 128. The proximal annular flange 144 also defines a proximal surface 144a and a distal surface 144b.

The proximal portion 140 includes at least one bendable rib 146 attached to the inner surface 140c of the proximal portion 140. In one embodiment, the rib 146 has an elongated shape with a distal end 146a and a proximal end 146b. The rib 146 extends longitudinally between the proximal end 140a and the distal end 140b of the proximal portion 140. The rib 146 comprises a bendable material such as metal or plastic, that allows the rib 146 to be easily folded outwardly or inwardly anywhere along its length. Once folded, the bendable material of the rib 146 maintains the rib 146 at its folded state without user intervention.

Figure 3:
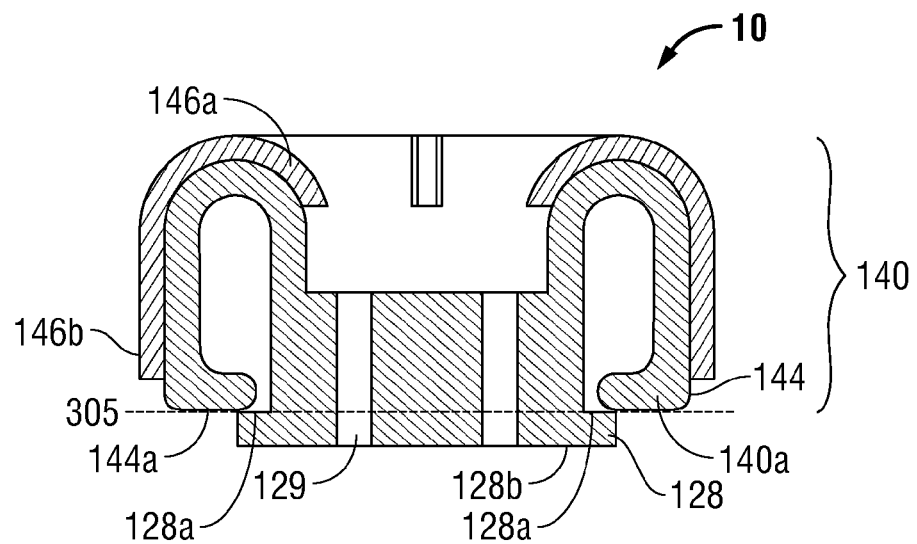
FIG. 3 is a side cross-sectional view of the surgical apparatus of FIG. 1 illustrating that the surgical apparatus is adjusted to accommodate a tissue with a minimum thickness.

FIG. 3 illustrates the situation when the rib 146 is folded outwardly at its distal end 146a which causes the proximal end 140a of the proximal portion 140 to propagate in a distal direction. As illustrated in FIG. 3, the proximal surface 144a of the proximal annular flange 144 becomes horizontally aligned with respect to the proximal surface 128a of the distal annular flange 128 with a negligible distance therebetween. The negligible distance between the two proximal surfaces 144a and 128a corresponds to the minimum tissue thickness that the surgical apparatus 10 can accommodate. As illustrated in FIG. 3, the tissue tract 305 is securely sandwiched between the two proximal surfaces 144a and 128a, receiving a downward pressure supplied by the proximal annular flange 144 and an upward pressure supplied by the distal annular flange 128.

Figure 4:
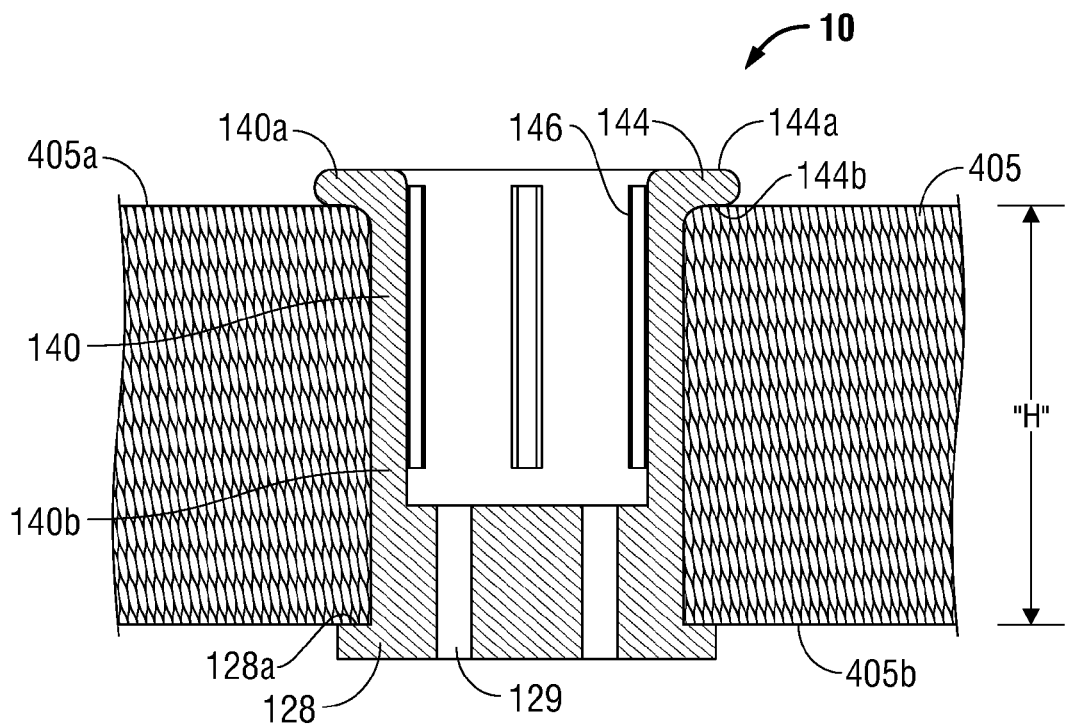
FIG. 4 is a side cross-sectional view of the surgical apparatus of FIG. 1 illustrating that the surgical apparatus is adjusted to accommodate a tissue with a maximum thickness.

FIG. 4 illustrates the situation where the proximal portion 140 is bent inwardly under the pressure of the surrounding tissue tract 405 that reduces the proximal annular flange 144 to the same radial dimension as that of the distal annular flange 128. As illustrated in FIG. 4, the surgical apparatus 10 snugly fits within the tissue tract 405 with the distal annular flange 128 disposed immediately beneath the tissue tract 405, and the proximal annular flange 144 disposed immediately above the tissue tract 405. Specifically, the proximal surface 128a of the distal annular flange 128 abuts the lower side 405b of the tissue tract 405 and the distal surface 144b of the proximal annular flange 144 abuts the upper side 405a of the tissue tract 405. The distance "H" between the proximal surface 128a of the distal annular flange 128 and the distal surface 144b of the proximal annular flange 144 represents the maximum tissue thickness that the surgical apparatus 10 can accommodate. The two annular flanges 144 and 128, due to their relatively large outer circumferences, securely hold the tissue tract 405 therebetween.

In view of FIGS. 3 and 4, the surgical apparatus 10 can accommodate tissues of different thicknesses varying from a minimum thickness, which is almost negligible as illustrated in FIG. 3, to a maximum thickness "H" as illustrated in FIG. 4.

In a certain embodiment, the surgical apparatus 10, except the rib 146, is made from a semi-resilient, disposable, compressible and flexible type (e.g. rubber or sponge) material, for example, but not limited to, a suitable foam, gel material, or soft rubber having sufficient compliance to form a seal about one or more surgical objects, and also establish a sealing relation with the tissue tract 105 and with the surgical object. In one embodiment, the foam includes a polyisoprene material. The flexible material easily adjusts the surgical apparatus 10 to different configurations under the influence of biasing factors, such as bending force supplied by the rib 146 as illustrated in FIG. 3 or pressure from the surrounding tissue tract 405 as illustrated in FIG. 4. Under the influence of biasing factors, the surgical apparatus 10 is adjusted from its normal, original shape, i.e., a generally frustoconical configuration, to a deformed shape as illustrated in FIG. 3 or a generally cylindrical configuration as illustrated in FIG. 4. The resilient material enables the surgical apparatus 10 to resume its normal, original shape in the absence of any biasing factors. The resilient material also provides an easy insertion and removal of the surgical apparatus 10 through the tissue tract 105.

In one embodiment, the rib 146 is an integrated part of the surgical apparatus 10. For instance, the rib 146 is permanently attached to the proximal portion 140 by adhesive or by an overmolding process.

Figure 5:
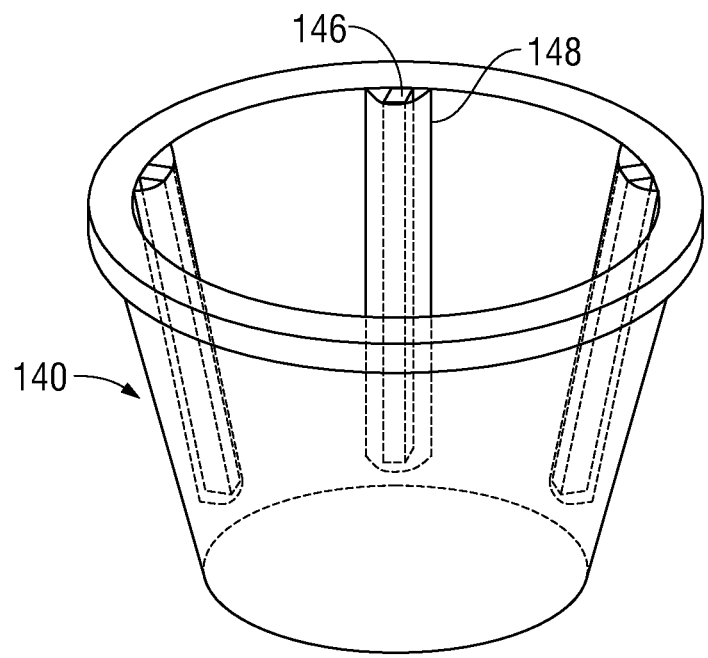
FIG. 5 illustrates one embodiment of the proximal portion that defines pockets for receiving ribs.

In another embodiment, the rib 146 is detachably connected to the proximal portion 140. For instance, as illustrated in FIG. 5, the proximal portion 140 defines at least one pocket 148 for reception of the rib 146. The proximal portion 140 may define a plurality of pockets 148 each configured to receive a rib 146. Since each pocket 148 is configured to removably receive a rib 146, ribs 146 of varying properties (e.g. different materials with different flexibilities) may be selectively chosen and inserted into the pockets 148 accordingly.

In one embodiment, it is envisioned that the pocket 148 is made from the same material as that of the proximal portion 140. It is also envisioned that the pocket 148 is an integrated part of the proximal portion 140.

In other embodiments, it is envisioned that the pocket 148 is made from a material different from that of the proximal portion 140.

In one embodiment, the surgical apparatus 10 includes a plurality of ribs 146. For instance, the surgical apparatus 10 may include four ribs 146.

In other embodiments, the surgical apparatus 10 has at least one bendable strip or bendable tube, in lieu of rib 146. For instance, the surgical apparatus 10 may include four bendable strips or four bendable tubes, in lieu of four ribs 146.

Figure 6:
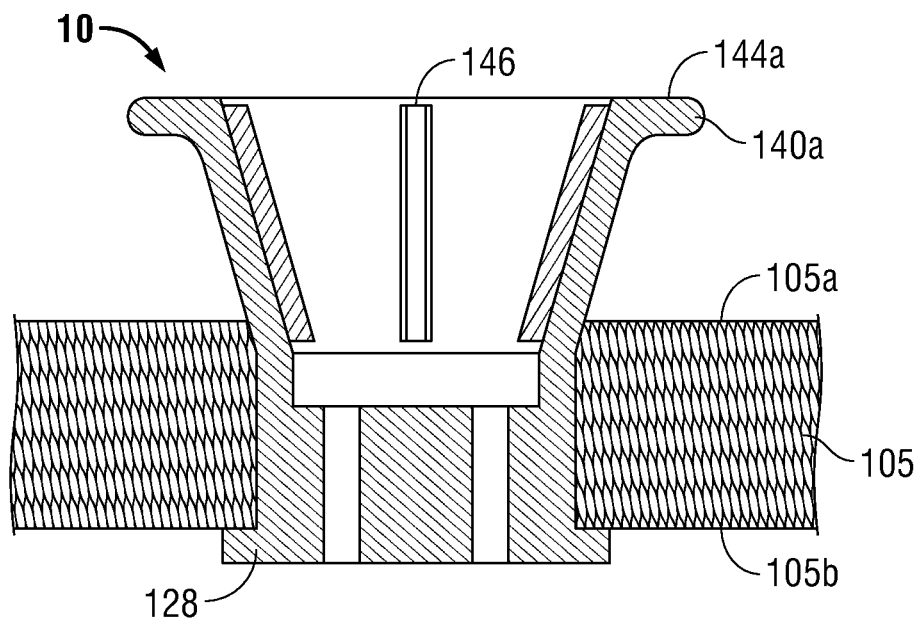
FIG. 6 is a side cross-sectional view of the surgical apparatus of FIG. 1 illustrating the surgical apparatus disposed within a tissue.
Figure 7:
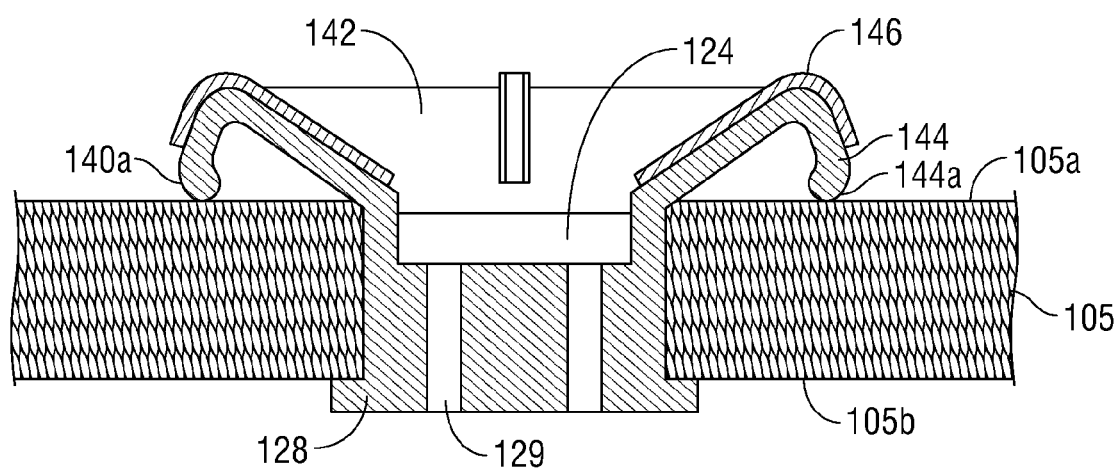
FIG. 7 is a side cross-sectional view of the surgical apparatus of FIG. 6 illustrating the proximal portion bent to approximate the tissue thickness.

FIGS. 6 and 7 illustrate the operation of the surgical apparatus 10. As illustrated in FIG. 6, the surgeon introduces the surgical apparatus 10 into the tissue tract 105 with the distal annular flange 128 disposed immediately beneath the lower side 105b of the tissue tract 105. As illustrated in FIG. 7, the surgeon folds the rib 146 outwardly to the extent that the proximal end 140a of the proximal portion 140 touches the upper side 105a of the tissue tract 105. The rib 146 is folded or bent to the extent that the proximal surface 144a of the proximal annular flange 144 presses against the upper side 105a of the tissue tract 105. The surgeon introduces one or more surgical instrument into the longitudinal passages 129 of the surgical apparatus 10 to conduct a minimally invasive procedure.

In use, the surgical apparatus 10 can adapt to tissues having different tissue thickness. Specifically, the surgical apparatus 10 can approximate a tissue having a thickness anywhere between a negligible thickness as illustrated in FIG. 3 and a maximal thicknesses "H" as illustrated in FIG. 4. The frustoconical-shaped proximal portion 140 readily allows the rib 146 to be folded or bent in an outward fashion, and thereby increases ease of adjusting the surgical apparatus 10 to different tissue thicknesses. Throughout the course of the procedure, the rib 146 maintains the surgical apparatus 10 at its adjusted position, and the annular flanges 144 and 128 securely hold the tissue therebetween.

Further, the frustoconical-shaped free space 142 defined by the proximal portion 140 and the cylindrically-shaped free space 124 defined by the ring member 122 promote a significantly increased range of motion of any surgical instrument inserted through the surgical apparatus 10, and greatly facilitates off-axis motions of the surgical instrument. More importantly, the free spaces 142 and 124 increase maneuverability of multiple instruments that are simultaneously operated through the surgical apparatus 10.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Different embodiments of the disclosure may be combined with one another based on the particular needs of the patients to achieve optimal results of the surgical procedures. Those skilled in the art will envision other modifications within the scope and spirit of the claims appended hereto.

What is claimed is:

1. A surgical apparatus for positioning within a tissue tract accessing an underlying body cavity, which comprises:
   a proximal portion defining a continuous tubular wall bendable by a user between an initial position and a bent position;
   a compressible distal portion disposed distally with respect to the proximal portion and defining a plurality of longitudinal passages through the compressible distal portion, wherein the compressible distal portion includes a distal annular flange; and
   a plurality of bendable structures attached to the proximal portion extending between a first end and a second end of the proximal portion, the plurality of bendable structures configured to maintain the proximal portion in the bent position until the user selectively returns the proximal portion towards its initial position.

2. The surgical apparatus according to claim 1, wherein each of the plurality of bendable structures is configured to fold along a length thereof.

3. The surgical apparatus according to claim 1, wherein the proximal portion defines a generally frustoconical configuration.

4. The surgical apparatus according to claim 1, wherein the proximal portion, in the bent position, shortens an overall length of the apparatus so as to assist in maintaining a seal with tissue surrounding the tissue tract.

5. The surgical apparatus according to claim 1, wherein folding at least one of the plurality of bendable structures causes the first end of the proximal portion to propagate in a distal direction.

6. The surgical apparatus according to claim 1, wherein each of the plurality of bendable structures is attached to the proximal portion by adhesive or by an overmolding process.

7. The surgical apparatus according to claim 1, wherein the proximal portion defines at least one pocket to detachably receive at least one of the plurality of bendable structures.

8. The surgical apparatus according to claim 1, wherein each of the plurality of bendable structures is in the form of a rib, strip or tube.

9. The surgical apparatus according to claim 1, wherein each of the plurality of bendable structures is made from a bendable material.

10. The surgical apparatus according to claim 9, wherein the bendable material is metal.

11. The surgical apparatus according to claim 9, wherein the bendable material is plastic.

12. The surgical apparatus according to claim 1, wherein the compressible distal portion includes a ring member having an annular configuration.

13. The surgical apparatus according to claim 12, wherein the compressible distal portion further includes a base member disposed distally with respect to the ring member.

14. The surgical apparatus according to claim 1, wherein at least one of the plurality of bendable structures defines an elongated shape.

15. A surgical apparatus for positioning within a tissue tract accessing an underlying body cavity, which comprises:
 a ring member defining an annular configuration;
 a proximal portion defining a continuous tubular wall disposed proximally with respect to the ring member;
 a compressible base member disposed distally with respect to the ring member and defining a plurality of longitudinal passages through the compressible base member, wherein the compressible base member includes a distal annular flange; and
 a plurality of bendable elongated ribs attached to the proximal portion extending between a first end and a second end of the proximal portion.

16. The surgical apparatus according to claim 15, wherein at least one of the plurality of bendable elongated ribs is configured to fold along its length.

17. The surgical apparatus according to claim 15, wherein folding at least one of the plurality of bendable elongated ribs causes the first end of the proximal portion to propagate in a distal direction.

18. The surgical apparatus according to claim 15, wherein the proximal portion defines a generally frustoconical configuration.

* * * * *